Figure 3A:
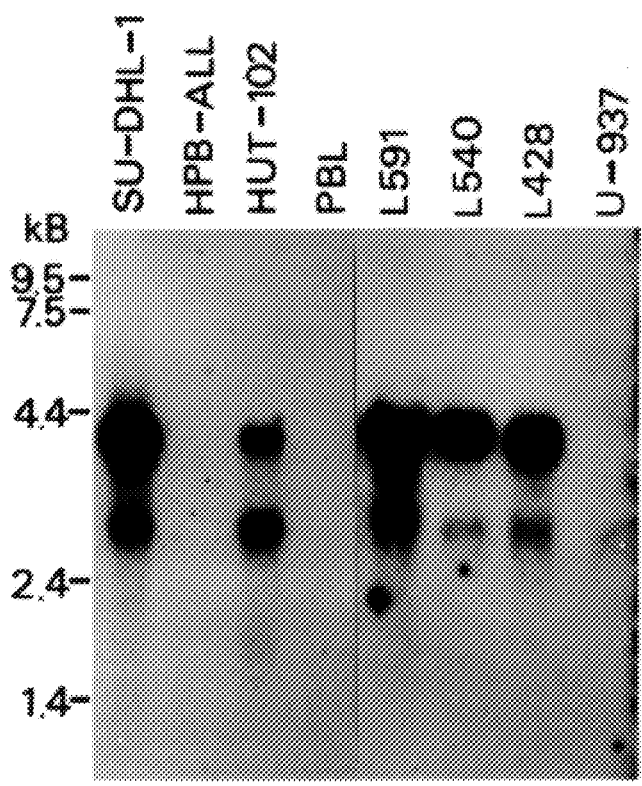

United States Patent [19]
Stein et al.

[11] Patent Number: 5,866,372
[45] Date of Patent: *Feb. 2, 1999

[54] NUCLEIC ACIDS ENCODING LYMPHOID CD30 ANTIGEN

[76] Inventors: Harald Stein, Balbronner Str. 3, D-1000 Berlin 33; Horst Dürkop, Krumme Str. 70, D-1000 Berlin 12; Ute Latza, Wundstr. 62, D-1000 Berlin 19, all of Germany

[ * ] Notice: This patent issued on a continued prosecution application filed under 37 CFR 1.53(d), and is subject to the twenty year patent term provisions of 35 U.S.C. 154(a)(2).

[21] Appl. No.: 232,087

[22] PCT Filed: Nov. 16, 1992

[86] PCT No.: PCT/DE92/00956

§ 371 Date: Sep. 8, 1994

§ 102(e) Date: Sep. 8, 1994

[87] PCT Pub. No.: WO93/10232

PCT Pub. Date: May 27, 1993

[30] Foreign Application Priority Data

Jan. 2, 1991 [DE] Germany .......................... 42 00 043.2
Nov. 15, 1991 [DE] Germany .......................... 41 37 716.8

[51] Int. Cl.[6] .............................. C12N 15/12; C07H 21/04
[52] U.S. Cl. ........................ 435/69.3; 435/69.7; 435/325; 435/252.3; 435/320.1; 536/23.5; 536/24.31; 935/12

[58] Field of Search .................................. 536/23.1, 23.4, 536/23.5, 24.31; 435/69.1, 69.7, 69.3, 172.1, 172.3, 240.2, 252.3, 320.1, 325, 362; 530/350, 403; 935/9, 10, 12

[56] References Cited

PUBLICATIONS

M.A. Frohman et al., PNAS 85:8998–9002, Dec. 1988.
H. Durkop et al., Cell 68:421–427, Feb. 7, 1992.
P. Froese et al., J. Immunology 139(6):2081–2087, Sep. 15, 1987.
O. Josimovik–Alasevik et al., Eur. J. Immunol. 19:157–162, 1989.
A. Aruffo et al., PNAS 84:8573–8577, 1987.
R.A. Young et al., PNAS 80:1194–1198, 1983.

*Primary Examiner*—Lorraine Spector
*Attorney, Agent, or Firm*—Birch, Stewart, Kolasch & Birch, LLP

[57] ABSTRACT

The description relates to the lymphoid surface antigen CD30 (Ki-1) occurring in Hodgkin's disease, the protein sequence and the associated nucleotide sequence therein, manufacture thereof by genetic engineering, methods for diagnosis and investigation of Hodgkin's disease and use of these nucleotide sequences for producing transgenic animals. The invention provides methods not based on monoclonal antibodies for investigation and diagnosis of anaplastic large-cell lymphomas.

32 Claims, 13 Drawing Sheets

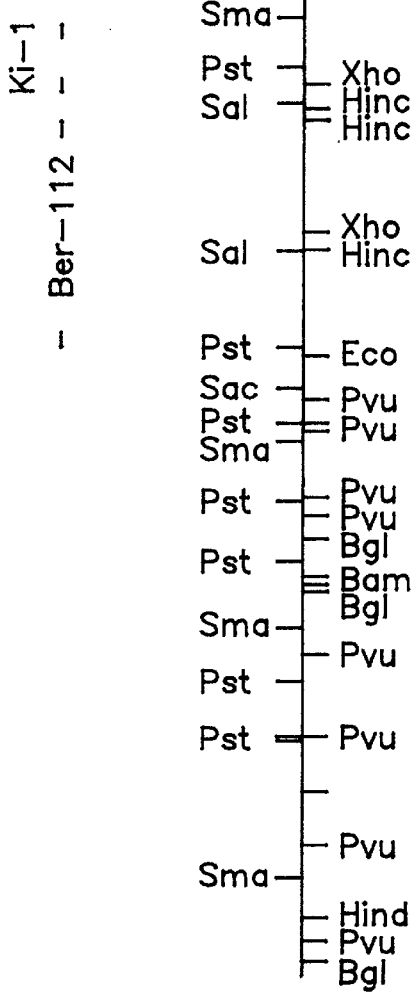
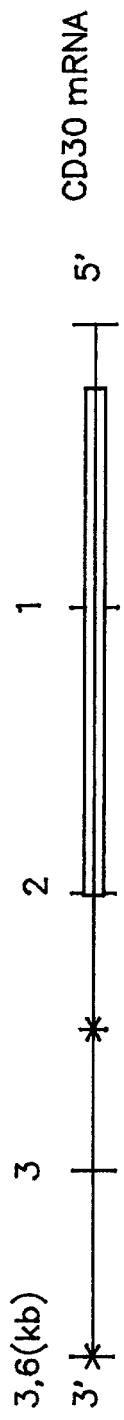
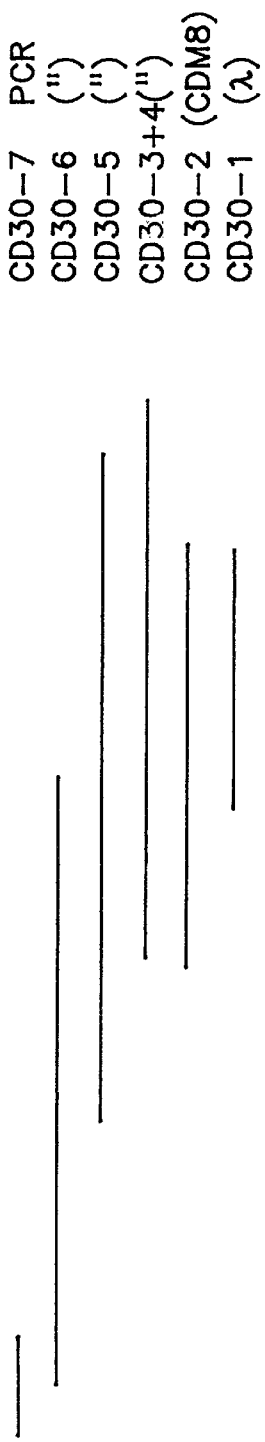
FIG. 1D  Epitope of mAB
FIG. 1C  Restriction enzyme
FIG. 1B  CD30 mRNA
FIG. 1A

Fig. 2A

```
                                     30
ATA CGG GAG AAC TAA GGC TGA AAC CTC GGA GGA ACA ACC

60
ACT TTT GAA GTG ACT TCG CGG CGT GCG TTG GGT GCG GAC

90
TAG GTG GCC CCG GCG GGA GTG TGC TGG AGC TGA AGT CC 120                                                  150
ACG CGC GCG GCT GAG AAC CGC CGG GAC CGC ACG TGG GCG

180
CCG CGC GCT TCC CCC GCT TCC CAG GTG GGC GCC GGC CGC

210
CAG GCC ACC TCA CGT CCG GCC CCG GGG ATG CGC GTC CTC
                                     Met Arg Val Leu 240                                          270
CTC GCC GCG CTG GGA CTG CTG TTC CTG GGG GCG CTA CGA
Leu Ala Ala Leu Gly Leu Leu Phe Leu Gly Ala Leu Arg

300
GCC TTC CCA CAG GAT CGA CCC TTC GAG GAC ACC TGT CAT
Ala Phe Pro Gln Asp Arg Pro Phe Glu Asp Thr Cys His

★               330
GGA AAC CCC AGC CAC TAC TAT GAC AAG GCT GTC AGG AGG
Gly Asn Pro Ser His Tyr Tyr Asp Lys Ala Val Arg Arg 360                                          390
TGC TGT TAC CGC TGC CCC ATG GGG CTG TTC CCG ACA CAG
Cys Cys Tyr Arg Cys Pro Met Gly Leu Phe Pro Thr Gln

420
CAG TGC CCA CAG AGG CCT ACT GAC TGC AGG AAG CAG TGT
Gln Cys Pro Gln Arg Pro Thr Asp Cys Arg Lys Gln Cys

TYR TYR       450
GAG CCT GAC TAC TAC CTG GAT GAG GCC GAC CGC TGT ACA
Glu Pro Asp Tyr Tyr Leu Asp Glu Ala Asp Arg Cys Thr
```

Fig. 2B

```
              480
GCC TGC GTG ACT TGT TCT CGA GAT GAC CTC GTG GAG AAG
Ala Cys Val Thr Cys Ser Arg Asp Asp Leu Val Glu Lys

510                  ★                          540
ACG CCG TGT GCA TGG AAC TCC TCC CGT GTC TGC GAA TGT
Thr Pro Cys Ala Trp Asn Ser Ser Arg Val Cys Glu Cys

570
CGA CCC GGC ATG TTC TGT TCC ACG TCT GCC GTC AAC TCC
Arg Pro Gly Met Phe Cys Ser Thr Ser Ala Val Asn Ser

600
TGT GCC CGC TGC TTC TTC CAT TCT GTC TGT CCG GCA GGG
Cys Ala Arg Cys Phe Phe His Ser Val Cys Pro Ala Gly 630                                   660
ATG ATT GTC AAG TTC CCA GGC ACG GCG CAG AAG AAC ACG
Met Ile Val Lys Phe Pro Gly Thr Ala Gln Lys Asn Thr

690
GTC TGT GAG CCG GCT TCC CCA GGG GTC AGC CCT GCC TGT
Val Cys Glu Pro Ala Ser Pro Gly Val Ser Pro Ala Cys

720
GCC AGC CCA GAG AAC TGC AAG GAA CCC TCC AGT GGC ACC
Ala Ser Pro Glu Asn Cys Lys Glu Pro Ser Ser Gly Thr 750                                           780
ATC CCC CAG GCC AAG CCC ACC CCG GTG TCC CCA GCA ACC
Ile Pro Gln Ala Lys Pro Thr Pro Val Ser Pro Ala Thr

810
TCC AGT GCC AGC ACC ATG CCT GTA AGA GGG GGC ACC CGC
Ser Ser Ala Ser Thr Met Pro Val Arg Gly Gly Thr Arg

840
CTC GCC CAG GAA GCT GCT TCT AAA CTG ACG AGG GCT CCC
Leu Ala Gln Glu Ala Ala Ser Lys Leu Thr Arg Ala Pro
```

Fig. 2C

```
                870
GAC TCT CCC TCC TCT GTG GGA AGG CCT AGT TCA GAT CCA
Asp Ser Pro Ser Ser Val Gly Arg Pro Ser Ser Asp Pro 900                                         930
GGT CTG TCC CCA ACA CAG CCA TGC CCA GAG GGG TCT GGT
Gly Leu Ser Pro Thr Gln Pro Cys Pro Glu Gly Ser Gly

960     TYR TYR
GAT TGC AGA AAG CAG TGT GAG CCC GAC TAC TAC CTG GAC
Asp Cys Arg Lys Gln Cys Glu Pro Asp Tyr Tyr Leu Asp

990
GAG GCC GGC CGC TGC ACA GCC TGC GTG AGC TGT TCT CGA
Glu Ala Gly Arg Cys Thr Ala Cys Val Ser Cys Ser Arg 1020                                    1050
GAT GAC CTT GTG GAG AAG ACG CCA TGT GCA TGG AAC TCC
Asp Asp Leu Val Glu Lys Thr Pro Cys Ala Trp Asn Ser

1080
TCC CGC ACC TGC GAA TGT CGA CCT GGC ATG ATC TGT GCC
Ser Arg Thr Cys Glu Cys Arg Pro Gly Met Ile Cys Ala

1110
ACA TCA GCC ACC AAC TCC TGT GCC CGC TGT GTC CCC TAC
Thr Ser Ala Thr Asn Ser Cys Ala Arg Cys Val Pro Tyr 1140                                    1170
CCA ATC TGT GCA GCA GAG ACG GTC ACC AAG CCC CAG GAT
Pro Ile Cys Ala Ala Glu Thr Val Thr Lys Pro Gln Asp

1200
ATG GCT GAG AAG GAC ACC ACC TTT GAG GCG CCA CCC CTG
Met Ala Glu Lys Asp Thr Thr Phe Glu Ala Pro Pro Leu

1230
GGG ACC CAG CCG GAC TGC AAC CCC ACC CCA GAG AAT GGC
Gly Thr Gln Pro Asp Cys Asn Pro Thr Pro Glu Asn Gly
```

Fig. 2D

```
                    1260
GAG GCG CCT GCC AGC ACC AGC CCC  ACT CAG AGC TTG CTG
Glu Ala Pro Ala Ser Thr Ser Pro  Thr Gln Ser Leu Leu 1290                                         1320
GTG GAC TCC CAG GCC AGT AAG ACG CTG CCC ATC CCA ACC
Val Asp Ser Gln Ala Ser Lys Thr Leu Pro Ile Pro Thr

1350
AGC GCT CCC GTC GCT CTC TCC TCC ACG GGG AGG CCC GTT
Ser Ala Pro Val Ala Leu Ser Ser Thr Gly Lys Pro Val

1380
CTG GAT GCA GGG CCA GTG CTC TTC TGG GTG ATC CTG GTG
Leu Asp Ala Gly Pro Val Leu Phe Trp Val Ile Leu Val 1410                                      1440
TTG GTT GTG GTG GTC GGC TCC AGC GCC TTC CTC CTG TGC
Leu Val Val Val Val Gly Ser Ser Ala Phe Leu Leu Cys

1470
CAC CGG AGG GCC TGC AGG AAG CGA ATT CGG CAG AAG CTC
His Arg Arg Ala Cys Arg Lys Arg Ile Arg Gln Lys Leu

1500
CAC CTG TGC TAC CCG GTC CAG ACC TCC CAG CCC AAG CTA
His Leu Cys Tyr Pro Val Gln Thr Ser Gln Pro Lys Leu

1530                              AMP   1560
GAG CTT GTG GAT TCC AGA CCC AGG AGG AGC TCA ACG CAG
Glu Leu Val Asp Ser Arg Pro Arg Arg Ser Ser Thr Gln

1590
CTG AGG AGT GGT GCG TCG GTG ACA GAA CCC GTC GCG GAA
Leu Arg Ser Gly Ala Ser Val Thr Glu Pro Val Ala Glu

1620
GAG CGA GGG TTA ATG AGC AGC CA CTG ATG GAG ACC TGC
Glu Arg Gly Leu Met Ser Gln Pro Leu Met Glu Thr Cys
```

Fig. 2E

```
           1650
CAC AGC GTG GGG GCA GCC TAC CTG GAG AGC CTG CCG GTG
His Ser Val Gly Ala Ala Tyr Leu Glu Ser Leu Pro Leu

1680                                    CK2 PKC
CAG GAT GCC AGC CCG GCC GGG GGC CCC TCG TGG CCC AGG
Gln Asp Ala Ser Pro Ala Gly Gly Pro Ser Ser Pro Arg

1740
GAC CTT CCT GAG CCC CGG GTG TCC ACG GAG CAC ACC AAT
Asp Leu Pro Glu Pro Arg Val Ser Thr Glu His Thr Asn

1770                                 PKC
AAC AAG ATT GAG AAA ATC TAC ATC ATG AAG GCT GAC ACC
Asn Lys Ile Glu Lys Ile Tyr Ile Met Lys Ala Asp Thr 1800                                    1830
GTG ATC GTG GGG ACC GTG AAG GCT GAG CTG CCG GAG GGC
Val Ile Val Gly Thr Val Lys Ala Glu Leu Pro Glu Gly

1860
CGG GGC CTG GCG GGG CCA GCA GAG CCC GAG TTG GAG GAG
Arg Gly Leu Ala Gly Pro Ala Glu Pro Glu Leu Glu Glu

1890
GAG CTG GAG GCG GAC CAT ACC CCC CAC TAC CCC GAG CAG
Glu Leu Glu Ala Asp His Thr Pro His Tyr Pro Glu Gln

1920                  CK2              1950
GAG ACA GAA CCG CCT CTG GGC AGC TGC AGC GAT GTC ATG
Glu Thr Glu Pro Pro Leu Gly Ser Cys Ser Asp Val Met

CK2                              1980
CTC TCA GTG GAA GAG GAA GGG AAA GAA GAC CCC TTG CCC
Leu Ser Val Glu Glu Glu Gly Lys Glu Asp Pro Leu Pro

PKC        2010
ACA GCT GCC TCT GGA AAG TGA GGC CTG GGC TGG GCT GGG
Thr Ala Ala Ser Gly Lys End
```

Fig. 2F

```
                    2040
      GCT AGG AGG GCA GCA GGG TGG CCT CTG GGA GGC AGG GAT 2070                                    2100
      GGC ACT GTT GGC ACC GAG GTT GGG GGC AGA GGC CCA TCT

2130
      GGC CTG AAC TGA GGC TCC AGC ATC TAG TGG TGG ACC GGC

2160
      CGG TCA CTG CAG GGG TCT GGT GGT CTC TGC TTG CAT CCC 2190                                 2220
      CAA CTT AGC TGT CCC CTG ACC CAG AGC CTA GGG GAT CCG

2250
      GGG CTT GTA CAG AAG AGA CAG TCC AAG AGG CAG CAA ACA

2310
      GAT GGC AGG ATG GGC ACT GCC GAG AAC AGC ATT GGT CCC 2340                                 2370
      AGA GCC CTG GGC ATC AGA CCT TAA CCA CCA GGC CCA CAG

2400
      CCC AGC GAG GGA GAG GTC GTG AGG CCA GCT CCC GGG GCC

2430
      CCT GTA ACC CTA CTC TCC TCT CTC CCT GGA CCT CAG AGG

2460
      TGA CAC CCA TTG GGC CCT TCC GGC ATG CCC CCA GTT ACT 2490                                      2520
      GTA AAT GTG GCC CCC AGT GGG CAT GGA GCC AGT GCC TGT

2550
      GGT TGT TTC TCC AGA GTC AAA AGG GAA GTC GAG GGA TGG

2580
      GGC GTC GTC AGC TGG CAC TGT CTC TGC TGC AGC GGC CAC
```

Fig. 2G

```
     2610                                              2640
ACT GTA CTC TGC ACT GGT GTG AGG GCC CCT GCC TGG ACT

2670
GTG GGA CCC TCC TGG TGC TGC CCA CCT TCC CTG TCC TGT

2700
AGC CCC CTC GGT GGG CCC AGG GCC TAG GGG CCC AGG ATC 2730                                         2760
AAG TCA CTC ATC TCA GAA TGT CCC CAC CAA TCC CCG CCA

2790
CAG CAG GCG CCT CGG GTC CCA GAT GTC TGC AGC CCT CAG

2280
CAG CTG CAG ACC GCC CCT CAC CAA CCC AGA GAA CCT GCT

2850
TTA CTT TGC CCA GGG ACT TCC TCC CCA TGT GAA CAT GGG 2880                                         2910
GAA CTT CGG GCC CTG CCT GGA GTC CTT GAC CGC TCT CTG

2940
TGG GCC CCA CCC ACT CTG TCC TGG GAA ATG AAG AAG CAT

2970
CTT CCT TAG GTC TGC CCT GCT TGC AAA TCC ACT AGC ACC 3000                                         3030
GAC CCC ACC ACC TGG TTC CGG CTC TGC ACG CTT TGG GGT

3060
GTG GAT GTC GAG AGG CAC CAC GGC CTC ACC CAG GCA TCT

3090
GCT TTA CTC TGG ACC ATA GGA AAC AAG ACC GTT TGG AGG 3120                                     3150
TTT CAT CAG GAT TTT GGG TTT TTC ACA TTT CAC GCT AAG
```

Fig. 2H

```
                                    3180
GAG TAG TGG CCC TGA CTT CCG GTC GGC TGG CCA GCT GAC

3210
TCC CTA GGG CCT TCA GAC GTG TAT GCA AAT GAG TGA TGG

3240
ATA AGG ATG AGT CTT GGA GTT GCG GGC AGC CTG GAG ACT 3270                                        3300
CGT GGA CTT ACC GCC TGG AGG CAG GCC CGG GAA GGC TGC

3330
TGT TTA CTC ATC GGG CAG CCA CGT GCT CTC TGG AGG AAG

3360
TGA TAG TTT CTG AAA CCG CTC AGA TGT TTG GGA AGT 3390                                        3420
TGG AGA AGC CGT GGC CTT GCG AGA GGT GGT TAC ACC AGA

3450
ACC TGG ACA TTG GCC AGA AGA AGC TTA AGT GGG CAG ACA

3480
CTG TTT GCC CAG TGT TTG TGC AAG GAT GGA GTG GGT GTC 3510                                    3540
TCT GCA TCA CCC ACA GCC GCA GCT GTA AGG CAC GCT GGA

3570
AGG CAC ACG CCT GCC AGG CAG GGC AGT CTG GCG CCC ATG

3600
ATG GGA GGG ATT GAC ATG TTT CAA CAA AAT AAT GCA CTT

3622
CCT T(A)
```

FIG.5

NUCLEIC ACIDS ENCODING LYMPHOID CD30 ANTIGEN

This application is the U.S. National stage of PCT/DE92/00956, filed Nov. 16, 1992.

The invention relates to the lymphoid surface antigen CD30 occurring in Hodgkin's disease, its protein sequence and associated nucleotide sequence, manufacture thereof by genetic engineering, means for diagnosis and investigation of Hodgkin's disease and use of the nucleotide sequences, more particularly for producing transgenic animals.

The pathogenesis of Hodgkin's disease (HD) is as yet poorly understood, although in Central Europe it is numbered among the frequent human lymphomas. After the surface antigen CD30 had been described, identification of the tumour cells of Hodgkin's disease, i.e. the Hodgkin (H) and the Reed-Sternberg (RS) cells, became much easier or possible for the first time (Schwab et al (1982), Nature 299, 65–67; Stein et al (1982) Int. J. Cancer 30, 445–449; McMichael, publisher (1987): Leucocyte Typing III, Oxford University Press, Oxford). The appearance of the CD30 surface antigen is associated with activation of the lymphocytes, as shown by research on in vitro stimulated or virally (by HTLV-I, HTLV-II, EBV) transformed T and B cells (Stein et al, (1985) Blood, 66, 848–858; Andreesen et al. (1984) Blood, 63, 1299–1302). It is assumed that Hodgkin and Reed-Sternberg cells are malignant transformed T or B cells and that the histological variants in Hodgkin's disease are due to secretion of different cytokines (Stein et al. (1989) Recent Results Cancer Res.117, 15–26). The CD30 antigen therefore seems to be important as regards the intracellular signal system and the genesis of tumours.

Histological investigation of tumour tissues has also shown that the CD30 antigen is suitable for identification of large-cell anaplastic neoplasms, which are therefore also called CD30 or Ki-1-positive anaplastic large-cell lymphomas (ALCL; in English, Ki-1$^+$ anaplastic large cell lymphomas). These tumours, which occur particularly in children and young people, constitute a separate species of lymphomas and are called true histiocytic lymphomas or malignant histiocytosis. The simultaneous occurrence of re-arranged Ig and T-cell receptor genes in most CD30 positive ALCLs shows that these tumour cells are lymphoid. Accordingly, CD30-positive ALCLs are not only a phenotypic but also a genotypic unit. CD30-positive ALCLs are classified as primary and secondary; they originate mainly from T-cells and neutral cells, or to a lesser extent from B-cells. Morphologically, ALCLs are classified as a) common; b) Hodgkin-related; c) giant cell-rich and d) lympho-histiocytic.

Hitherto, by definition, the CD30 antigen has been detectable only by monoclonal antibodies, more particularly the monoclonal antibodies Ki-1 and Ber-H2 (Schwab et al. (1982) Nature 299, 65–67; Schwarting et al (1989) Blood 74, 1678–1689). One disadvantage, however, is that they only recognise a respective epitope on the antigen; they are also unsuitable for detecting and investigating the associated nucleic acids. A diagnosis based only on individual epitopes is also sensitive to artifacts and is not comprehensive. Finally, the recognisability of an isotope depends on how the sample is fixed and prepared; also the epitopes can alter with the state of the cell. For example an epitope can be blocked by glycosylation of neighbouring N- or O-glycosylation sites, and also phosphorylation, more particularly tyrosine phosphorylation, etc., bring about conformation changes which cause an epitope to disappear, particularly if it is made up of a number of peptide-chain portions. Such changes in cell state occur particularly often during the progress of the tumour.

Hitherto also it has been impossible to make a detailed investigation of the properties of the CD30 antigen as a receptor or binding protein with regard to other growth or hormonal factors—partly because of the small quantities available and also because the antigen is a membrane protein with functionally different cytosolic, transmembrane and extracellular protein portions, hereinafter also called domains.

The object of the invention therefore is to provide means, not based on monoclonal antibodies, for investigation, diagnosis and treatment of Hodgkin's disease and anaplastic large-cell lymphomas. More particularly the object is to provide methods of investigating the protein functions, the development of tumours, and means for treating these diseases.

This problem is solved by an isolated nucleic acid—a DNA or RNA—which can be hybridised with the nucleotide sequence for the human lymphocyte activation antigen CD30 shown in FIG. 2 SEQ ID NO:1. More particularly the problem is solved by a DNA or RNA containing a sequence of the nucleotide sequence shown in FIG. 2.

The nucleic acid according to the invention can have modifications detectable by laboratory analysis, e.g. radioactive atoms, fluorescent stain groups (Hawkins & Sulston (1990) Technique, Dec. 307) and/or introduced epitopes for light-based systems for detection of nucleic acids. In a preferred embodiment, the nucleic acids according to the invention can be bonded to a macroscopic carrier, such as beads, more particularly glass or Sepharose bodies, membrane filters, nitrocellulose filters or nylon filters, in order inter alia more easily to isolate or concentrate CD30-RNA by hybridisation.

The invention also relates to cloning vectors containing an aforementioned DNA sequence. Particularly suitable cloning vectors include those whereby the nucleic acids according to the invention can be amplified, e.g. pBR322, pUR101, M13mp10, M13mp11, M13mp18, M13mp19, pGEM1, etc., or vectors for protein expression of the cloned DNA sequences in the host cells, e.g. lambda gt11, pATH, etc., or vectors which temporarily transform prokaryotic or eucaryotic host cells, e.g. PCDM8 or derivatives or pRC/CMV, etc., or vectors which transform eucaryotic host cells in stable manner and integrate into the host genome, e.g. pXT1, etc., or vectors suitable for integration in the genome of germ cells and thus for producing transgenic animals, e.g. pSV2Neo, pRSVNeo, pMC1Neo, etc., The teaching according to the invention also covers host cells which express CD30 antigen SEQ ID NO:2, a fragment of the CD30 antigen, a hybrid protein with CD30 antigen or mutations thereof, more particularly eucaryotic host cells which incorporate CD30 antigen in the outer cell membrane or provide it with post-translational modifications, e.g. glycosylate the CD30 antigen in natural manner or provide it with complex sugar molecules, e.g. the COS cells described in Example 3 or L929 cells, RK13 cells, WOP cells or R9ab cells.

In an embodiment of the invention, the aforementioned CD30 molecules produced by recombinant DNA methods are preferably immunogens for producing polyclonal and monoclonal antibodies against the lymphoid CD30 surface antigen. For example a hybrid protein with β-galactosidase and CD30 antigen fragments can be isolated from lambda-gt-11 clones described hereinafter and used as an immunogen. The aforementioned method can also be used to express CD30 antigen in eucaryotic cells and use it for immunisation, after purification or as a protein in the membrane together with the over-expressing cell. Also, CD30 peptides corresponding to the protein sequence shown in FIG. 2 can be synthesised by chemical means, optionally coupled by glutaraldehyde or another coupling reagent to a suitable carrier, e.g. thyreoglobulin or albumin, and injected as an immunogen together with Freund adjuvant into a suitable animal, such as a mouse, rabbit, goat or sheep. CD30 (hybrid) molecules produced by biological or chemical synthesis are also suitable for use in the so-called "sandwich immuno-absorption" test.

According to another feature of the invention, pharmacologically relevant parts of CD30 are also made manifest by a knowledge of the nucleotide and protein sequence. Of particular pharmacological importance are the extracellular regions of the CD30 molecule, since ligand molecules to CD30 administered for therapeutic purposes naturally become bound first to the extracellular part of the membrane protein. The extracellular regions of CD30, as shown by comparative studies, the hydropathy curve and in vitro transcription and translation investigations, are coded mainly by the cDNA sequence between position 277 and position 1359, i.e. the sequence between $^{277}$-TTCCCACAGGATCGACCC . . . (SEQ ID NO:3) and . . . CTCCCACGGGGAAG$_{1359}$(SEQ ID NO:4). It is therefore an obvious idea to use these regions of the CD30 molecule or sub-sections thereof in particular for development of therapeutic agents. In particular, fusion proteins with original extracellular CD30 portions are particularly suitable for isolating or concentrating natural or synthetic immunotoxins against Hodgkin and Reed-Sternberg cells. Also, oligopeptides or recombinant peptides prepared on the basis of extracellular amino acid sequences of CD30 can be used as immunogens for producing polyclonal antibodies against extracellular CD30. Also, synthetic ligands to these protein sequences can be produced or developed. These ligands or antibodies can be coupled with a toxin, such as saponin or ricin A, so as to obtain therapeutically useful immunotoxins for treating these lymphomas. The application therefore also relates to use of the extracellular CD30 sequences for manufacture, search or isolation of binding partners, i.e. natural, already existing in vivo, or artificial, produced in vitro or induced in vivo, particularly ligands for producing immunotoxins. Special importance attaches to polyclonal antibodies against extracellular CD30 sequences, so that now for the first time polyclonal immunotoxins are available against Hodgkin's disease and anaplastic large-cell lymphomas. The extracellular CD30 peptide sequences can be produced by chemical synthesis, more particularly solid-phase peptide synthesis, or as recombinant fusion protein in prokaryotic and eucaryotic cells. Expression in yeasts and eucaryotic cells is preferred, particularly in insect cells or in tissue culture with fibroblasts, preferably human fibroblasts, since in that case the extracellular protein cells are glycosylated and modified partly in natural manner.

The invention also relates to use of the intracellular—cytosolic—protein sequences of CD30 which contribute to intracellular signal transduction. Clearly these sequences code for a portion of use for interaction with other proteins involved in additional signal transduction. The cytosolic part of the CD30 participating in intracellular signal transduction, as shown by comparative studies, the hydropathy curve and in vitro transcription and translation research, is mainly coded by the nucleotide sequence (see FIG. 2) between position 1444 and 2007, i.e. the sequence between $^{1444}$-CACCGGAGGGCCTGCA (SEQ ID NO:5) . . . and . . . CTGCCTCTGGAAAG-$_{2007}$ (SEQ ID NO:6). Another important aspect of this feature of the invention is the synthesis of recombinant CD30 protein (portions) with cytosolic activity, and development of ligands and bonding partners which influence the cytosolic activity of CD30.

The teaching according to the invention also covers use of the aforementioned nucleotide sequences for producing transgenic animals, more particularly rodents, with changed CD30 antigen expression, i.e. mutated, more particularly truncated CD30, over or under-expression of CD30, expression of CD30 in cells and tissues other than lymphocytes, complete absence of an intact structural gene for CD30, constitutive or inducible expression of CD30, or expression of CD30 at a predetermined site during differentiation of the cells. Such transgenic animals are excellent models for scientific research on lymphomas, development of clinical tests, or research into blocking and inductor molecules for the extracellular receptor part of the CD30 antigen.

Other preferred embodiments of the invention are described in the subsidiary and sub-claims.

The means and methods provided by the teaching according to the invention can now be used for detection of CD30 antigen-coding DNAs and RNAs by hybridisation or for localisation of the gene on the chromosome or chromosomes. It is therefore possible to investigate whether transcription of the CD30 gene has occurred in the cells in the sample, and also to investigate the regulation mechanisms for expression of the CD30 antigen.

In addition to these more scientific applications, the novel hybridisation methods—the PCR (polymerase chain) reaction, in-situ hybridisation on portions of tissue and chromosomes—provide an additional, very sensitive diagnosis. In particular, this diagnosis is not sensitive to post-translational modifications and processings.

Investigations on chromosomal localisation of the CD30 structural gene have at least shown that the gene lies in the chromosomal band 1p36, i.e. at a fragile place in the chromosome (see LeBeau (1986) Blood 67, 849–858) where chromosomal abnormalities including virus insertions (EBV, HTLVI and II, HV6 etc.) have already been detected in Hodgkin's disease and non-Hodgkin lymphomas and other neoplasias such as neuroblastomas and malignant melanomas. More particularly, in non- Hodgkin lymphomas, changes (duplication, translocations, deletions, etc.) occur in this chromosomal region and, together with expression of the CD30 antigen, are associated with particularly rapid growth of tumour. The nucleotide sequences provided by the invention are therefore excellent means for diagnosing whether these chromosomal changes have occurred in the patient and whether Hodgkin's disease or related large-cell anaplastic lyphomas are likely to occur.

The nucleotide sequences provided by the invention are also suitable for prenatal diagnosis, particularly when such diseases have already occurred in the family.

Figure 3B:
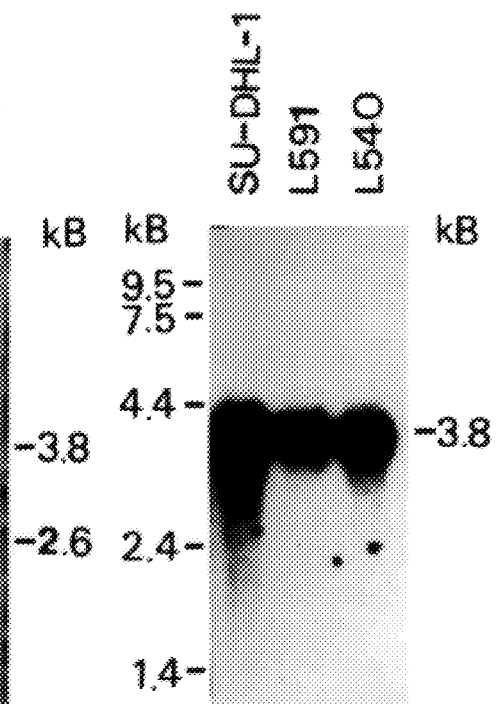
Figure 4:
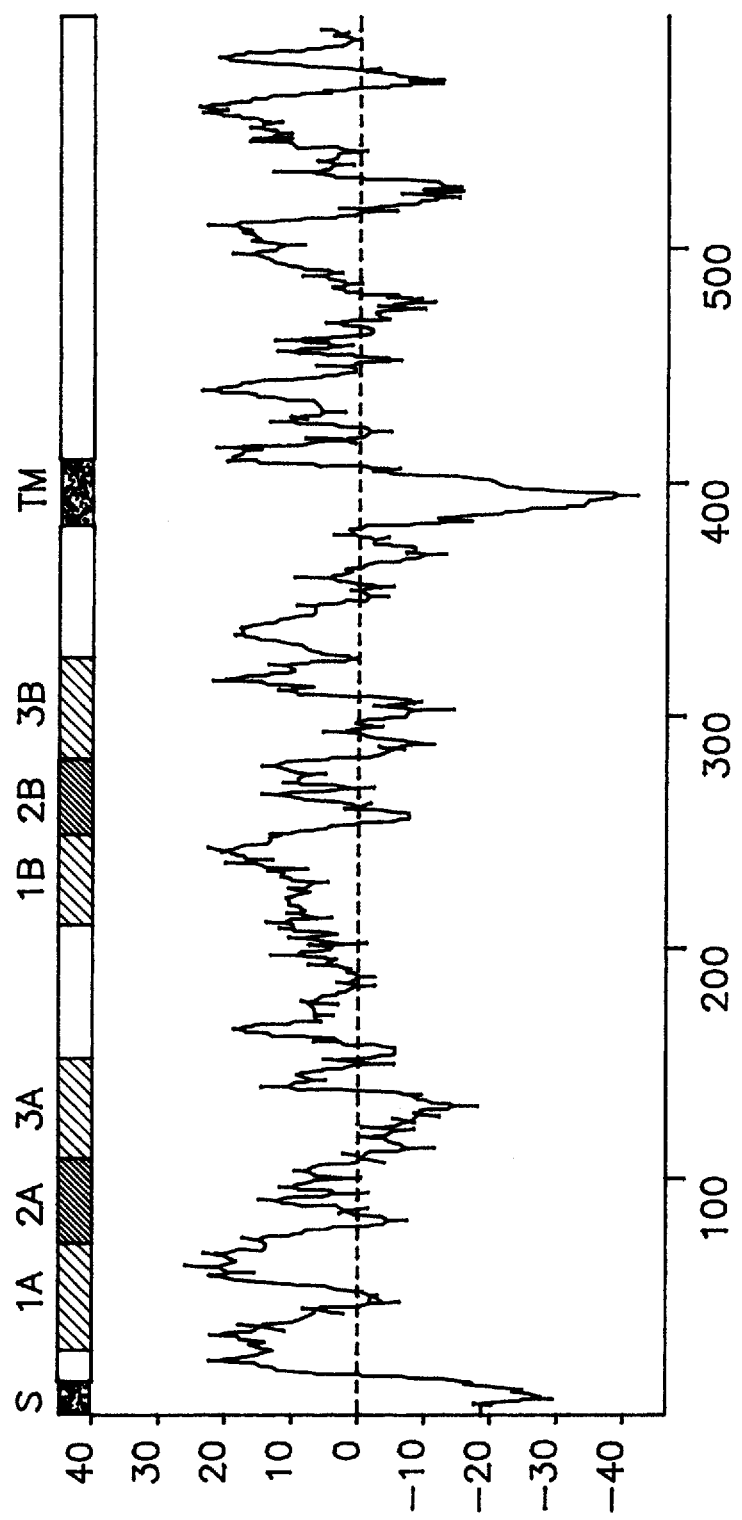

Other advantages, embodiments and features of the invention will be clear from the following description in conjunction with the drawings and diagrams, in which:

FIG. 1A) shows cloned CDNA portions of CD30 antigen mRNA in lambda gt11;

FIG. 1B) shows the regions (shaded rectangles) coding for the CD30 antigen on the mRNA and the non-coding regions (lines) with the polyadenylation sites (asterisks), FIG. 1C) is a restriction map of the cDNA with various restriction enzymes;

FIG. 1D) is a map of the CD30 antigen based on epitopes of the monoclonal antibodies Ki-1 and Ber-H2;

FIG. 2 parts A–H show the sequence of the non-transcribed strand of DNA, the coding strand of DNA and the CD30 protein sequence derivable therefrom;

FIG. 3 shows research into CD30-mRNAs in various human cell lines;

FIG. 4 is a diagram of the hydrophobic and hydrophilic properties of the CD30 amino acid sequence after Kyte & Doolittle (1982) J. Mol. Biol.157, 105–132;

FIG. 5 compares the CD30 sequence with sequences from the NGF receptor protein family. (SEQ ID NOS. 7–11)

Figure 6:
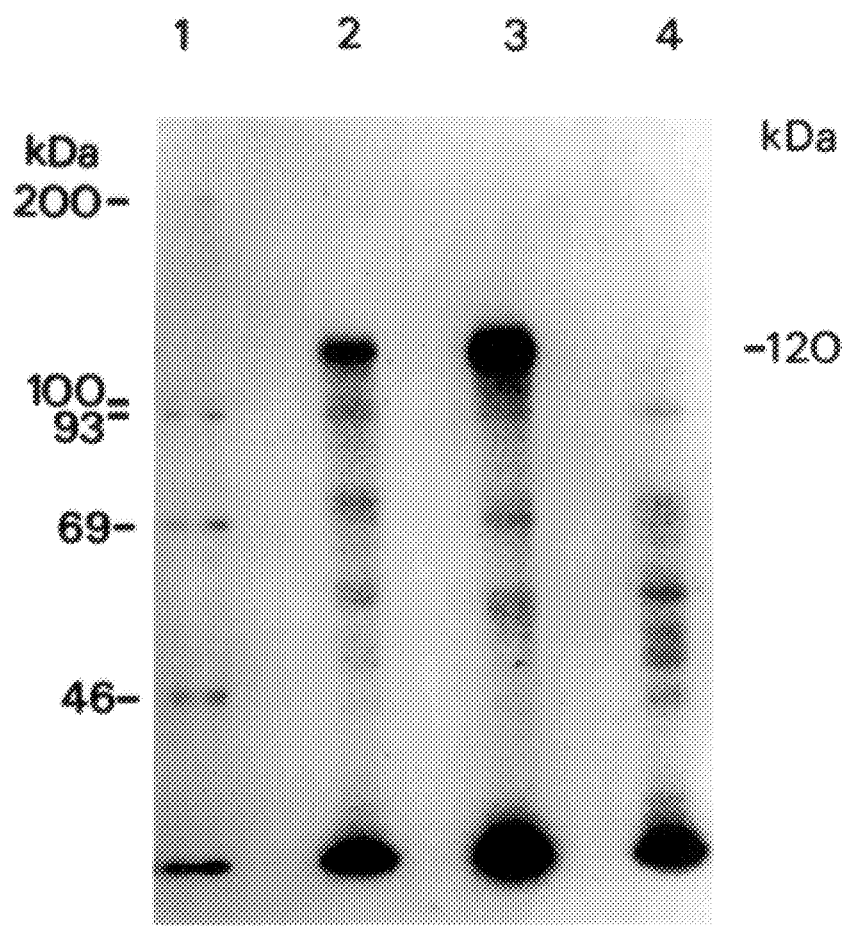

FIG. 6 shows expression of CD30 in COS cells.

immune precipitation of cells labelled with $^{125}J$:

track 1: marker proteins track 2: BER-H2 precipitate of CD30-5 transfected COS cells track 3: BER-H2 precipitate of HUT-102 cells track 4: BER-H2 precipitate of mock (PCDM8) transfected COS cells.

Cloning and Research into CD30-cDNA

A lambda-gt11-cDNA gene library of HUT-102 cells (Poiesz et al (1980) Proc. Natl. Acad. Sci. USA, 77, 7415–7419) comprising about 200 000 clones was tested with monoclonal antibodies for hybrid proteins with CD30 antigen.

cDNA synthesis based on poly(A)$^+$-RNA from HUT-102 cells was carried out after Guebler & Hoffmann (1983), Gene 25, 263–269. By way of variation, the cDNA was size-selected in a Sepharose-CL4B column (Eschenfeldt & Berger (1987) Methods in Enzymol.152, 335–337). Immunoscreening was performed with a mixture of the monoclonal antibody Ki-1 and Ber-H2 after Huynh et al (1985) in "DNA Cloning", A Practical Approach, Vol. 1, 49–78 (Published by D. M. Glover, IRL Press, Oxford, Washington D.C.).

A clone with a 909 bp CDNA produced a hybrid peptide which was recognised by the monoclonal antibody Ber-H2.

In order to obtain a clone containing the entire sequence for CD30, a pCDM8 gene library from HUT-102 cells was prepared (Seed & Aruffo (1987) Proc. Natl. Acad. Sci. USA 84, 3365–3369; Aruffo & Seed (1987) Proc. Natl. Acad. Sci. USA. 84, 8573–8577). The cDNA was synthesised using a cDNA synthesis kit produced by the company Invitrogen, then provided with BstXI linkers and finally size-fractionated on a 1.5% (w/v) Nu-Sieve gel made by the company FMC. cDNA with more than 1 kbp was isolated from the gel and ligated with the vector pCDM8. Transformation was brought about in E.coli- MC1061/p3 by electroporation after Dover et al (1988) Nucl. Acids. Res. 16, 6127–6145.

The colonies were hybridised by using the CD30-1-cDNA sample obtained by immunoscreening the lambda-gt11 library (T. Maniatis, E. F. Fritsch and J. Sambrook (1989) Molecular Cloning: A laboratory manual; Cold Spring Harbour Press, Cold Spring Harbour, New York). This approach yielded 5 clones overlapping in the cDNA sequences (FIG. 1) with 1492 bp (CD30-2), 1905 bp (CD30-3 and CD30-4), 2342 bp (CD30-5) and 2242 (CD30- 6). DNA was sequenced by using the Sequenase Sequencing Kit by the company US Biochemicals and synthetic oligonucleotide primers (Sanger et al (1977) Proc. Natl. Acad. Sci. USA, 74, 5463–5467).

In order to clone the 3'-poly(A) end also, a PCR reaction according to the RACE (rapid amplification of cDNA ends) protocol was brought about on reverse-transcribed poly(A) RNA from HUT-102 cells (Frohman et al (1988), Proc. Natl. Acad. Sci. USA, 85, 8998–9002). Amplification was brought about in 35 cycles comprising: 1 minute denaturing followed by 45 seconds addition of the primer at 54° C. and 1.5 minutes elongation at 72° C., with internal primers and oligo(dT) primers comprising a Sal1 site. The reaction was performed in 50 mM Tris HCl, pH 8.15, 6 mM MgCl$_2$, 40 mM KCl. This process yielded clone CD30-7 with a 333 bp cDNA.

The DNA of clone CD30-5 in vector pGEM1 was deposited, number DSM 6833, at the DSM (=German Collection of Microorganisms and Cell Cultures) in accordance with the Budapest Agreement.

The sequence of the CD30-cDNA and the protein sequence derivable therefrom are shown in FIG. 2. The signal peptide and the transmembrane domains are twice underlined. Polyadenylation signals are underlined once. The polyadenylation sites are marked by arrows. The homologous sub-units in the extracellular domains are enclosed in a frame, potential N-glycosylation sites are marked by asterisks, and potential phosphorylation sites are marked by the following abbreviations: TYR (tyrosine kinase), PKC (protein kinase C), CK2 (casein kinase II) and AMP (cAMP./cGMP-dependant kinase).

The complete nucleotide sequence of CD30-cDNA contains 3630 base pairs, the G/C content being 62%. The open reading frame goes from nucleotide 223 to nucleotide 2007—the termination codon. The ATG codon for initiation of translation is surrounded by typical start sequences (Kozak (1986) Cell 44, 283–292). The open reading frame consists of two 77% homologous approx. 360 bp domains (367–747 and 995–1272). The open reading frame is preceded by 230 base pairs of non-translated leader sequence, followed by 1613 base pairs of untranslated sequence with a short palindromic sequence between nucleotide 2867 and 2888. The unusually long 5' leader sequence is unnecessary for expression, since a cDNA without this sequence, e.g. from clone CD30-5 (see Example 3), can be expressed in COS cells.

The untranslated 3' region contains two sites for polyadenylation (marked by an arrow in FIG. 2), preceded by the unusual poly(A) signal sequences TGTAAA and AATAAT. (Birnstiel et al (1985) Cell 41, 349–359); Bardwell et al (1985) Cell 65, 125–133; Sheets et al (1990) Nucl. Acids. Res.18, 5799–5805).

Use of CD30 Nucleotide Sequences for Investigation of Cells, Tissues and Chromosomes

EXAMPLE 1

Northern blot analyses. The RNA from the cells and tissues was isolated by the guanidinium isothiocyanate-caesium chloride method of Chirgwin et al (1979) Biochemistry, 18, 5294–5299. The RNA was purified by an oligo(dT) cellulose column after Swan et al (1972) Proc. Natl. Acad. Sci. USA 69, 1408–1412. The resulting poly(A)$^+$ RNA was then separated by gel electrophoresis on a 1.2% (w/v) agarose gel with 2.2 mol/l formaldehyde—2 µg poly (A)$^+$ RNA per track—transferred to nitrocellulose membranes and then hybridised against $^{32}$P-dCTP labelled CD30 DNA inserts. The DNA was radioactively labelled by using a "DNA labelling kit" by Boehringer/Mannheim. Hybridisation was brought about by the method of Thomas (1977) Proc. Natl. Acad. Sci. USA, 77, 5201–5205.

FIGS. 3A and B show this kind of Northern blot analysis of RNA from the human cell lines HUT-102, SU-DHL-1 (Morgan et al (1989) Blood 73, 2155–2164), L-428 (Schaadt et al (1980) Int. J. Cancer 26, 723–731, L-591 (Diehl et al (1982) Cancer Treat. Rep.66, 615–632), L-540 (Diehl et al (1981) J. Cancer Res. Clin. Oncol.101, 111–124), Co (Jones et al. (1985) Hematol. Oncol.3, 133–145), Ho (Kamesaki et al (1986) Blood 68, 285–292), U-937 (Sundström & Nilsson (1976) Int. J. Cancer 17, 565–577), MDA-MB-231 (Cailleau et al. (1974) J. Nat. Cancer Inst. 53, 661–674) and HPB-ALL (Boylston & Cosford (1985) Eur. J. Immunol. 15, 738–742) and, for comparison, of PBL cells (peripheral blood lymphocytes)). The autoradiography lasted four days. The hybridisation sample was the CD30-5 insert with the coding region (FIG. 3A) and with the CD30-6 /Bgl1-Xba1 fragment of the non-translated 3' end (3B).

Two RNAs were detected in the cell lines under investigation, a larger RNA with about 3800 nucleotides and a smaller with about 2600 nucleotides. The RNAs probably originate from different splicing during polyadenylation.

The amount of CD30-coding RNA was greatest in the cell line SU-DHL-1 and in the cell line L-591 originating from a Hodgkin's lymphoma. It was followed by the cell lines L-540, L-428, Ho, Co originating from Hodgkin's lymphomas and finally by the cell line HUT-102 transformed by HTLV-1. Corresponding to the appearance of the CD30 antigen, no RNA transcripts were present in the peripheral blood lymphocytes or in the cell lines HPB-ALL, MDA-MB-231 or U-937. This shows the high specificity and sensitivity of the hybridisation sample.

EXAMPLE 2

Mapping of chromosomes. Isolated peripheral blood lymphocytes stimulated with PHA and from 2 healthy donors were blocked in culture by colchicine during cell division in the metaphase after Stollmann et al (1985), Br. J. Haematol. 60, 183–196 and the chromosomes were prepared, followed by in situ hybridisation after Fonatsch et al (1987), Cytogenet. Cell Genet. 45, 109–112 with the CD30-5/SmalcDNA fragment containing the sequence between the Smal site at position 218 and the Smal site at position 1732. The DNA was radioactively labelled by nick-translation with $^3$H-dCTP and $^3$H-dTTP. The specific activity of the sample was $1.2 \times 10^7$ dpm/$\mu$g DNA. Hybridization is performed in 2X SSC, 10% dextran sulfate and 50% formamide at 37° C. Washes are performed in 2X SSC, 50% formamide at 40° C., then in 2X SSC at room temperature. 99 metaphases were counted.

This research showed that the CD30 gene lies on the chromosome band 1p36. 21.6% of 162 silver grains lay specifically in this region. The chi-squared values are highly significant (P<0.001).

EXAMPLE 3

Expression of CD30 antigens in COS cells. To this end, COS cells were transfected with CD30-5-cDNA, after which the CD30 antigen was immune-precipitated from these cells. The expression vector used was the pCDM8 vector, in which the CD30-cDNA piece had been cloned. Transfection was brought about on COS-1 cells in cell culture by the DEAE dextran method (Seed & Aruffo (1987) Proc. Natl. Acad. Sci. USA, 84 3365–3369). 48 hours after transfection the cells were isolated, radioactively labelled with IODO beads (Messrs Pierce) and solubilised, and the proteins were immune-precipitated and separated by gel electrophoresis.

As a control, surface proteins from HUT-102 cells were radioactively labelled with IODO beads (produced by the company Pierce) and isolated by means of agarose beads coated with anti-mouse Ig (Schwarting et al (1989) Blood 74, 1678–1689).

FIG. 6 shows electrophoretic SDS gel analysis of CD30 immune-precipitated with monoclonal antibody Ber-H2. Track 1: control. Track 2: CD30-5-cDNA transfected COS cells. Track 3: From $^{125}$-labelled HUT-102 cells. Track 4: control—COS cells transfected with vector without insert. In all cases a single protein band with a relative molecular weight of 120 000 was found.

Immune-cytological APAAP (alkaline phosphatase antialkaline phosphatase) staining (Cordell et al (1984) J. Histochem. Cytochem. 32 219–229) was also carried out. This was a method of mapping the epitopes of monoclonal antibodies Ki-1 and Ber-H2 by comparison to show which monoclonal antibodies reacted with which hybrid proteins or truncated expressed protein, and was also a method of mapping the amino acid sequence derived from the cDNA map. The data from lambda gt11 immuno-screening and APAAP immune staining can be combined in order to localise the Ki-1 epitope in the extracellular domain (see FIG. 1D) between the amino terminus and the amino acid 93, and the Ber-H2 epitope is localised between the amino acids 112 and 416.

EXAMPLE 4

Expression of the CD30 antigen in rabbit cell lines RK13 and R9ab for immunising rabbits so as to produce polyclonal sera against CD30. To this end the cell lines were transfected with the vector pCDM8-CD30-5 or pRC/CMV-CD30-5 DEAE dextran. After transfection the cells were harvested and used to immunise rabbits in accordance with a suitable protocol.

EXAMPLE 5

Expression of the CD30 antigen in mouse fibroblast cell lines L929 and WOP for producing additional monoclonal antibodies with rats and mice against CD30. To this end the mouse fibroblasts were transfected with the vector pCDM8-CD30-5 or pRC/CMV-CD30-5 by the DEAE dextran method or by spheroblast fusion (Sandri-Goldrin et al Mol. Cell. Biol. 1 743–752). After transfection, mice or rats were immunised with the cells in accordance with a suitable protocol. In order to produce the hybridomas the spleens of the animals were prepared and the resulting lymphocytes were fused with a suitable mouse myeloma cell line (G. K öhler, C. Milstein, Nature (1975), 256, 495–497).

EXAMPLE 6

Use of CD30 antigen obtained by a recombinant method in RIAs, ELISAs, EIAs or similar immunodetection systems for measuring the soluble CD30 antigen occurring in sera during certain diseases. The CD30 for this purpose can be obtained by expression in eucaryotes or procaryotes, using the stated nucleic acid sequence, slightly modified if necessary. After affinity-chromatographic purification and determination of the CD30 content, these preparations can be used for standardisation of CD30 immunoassays.

The CD30 Peptide Sequence and the Resulting Possible Applications of the Invention A comparison involving the derived amino acid sequence for the CD30 antigen shows that the CD30 polypeptide is equivalent to other transmembrane growth factor receptors. More particularly the first and, to a lesser extent, the second cysteine-rich sub-unit in the extracellular domain is equivalent to the extracellular domains of other known receptors (see FIG. 5). The main similarities are with the human nerve growth factor receptor protein family, e.g. NGFR, TNFR-1, TNFR-II (Schall et al (1990) Cell 61, 361–370; Heller et al (1990) Proc. Natl. Acad. Sci. USA 87, 6151–6155; Loetscher et al (1990) Cell 61, 351–359; Kohno et al (1990) Proc. Natl. Acad. Sci. USA 87, 8331–8335; Engelmann et al (1990), J. Biol. Chem. 265, 1531–1536; Smith et al (1990) Science 248, 1019–1023) and the human nerve growth factor receptor (NGFR) of low affinity (Johnson et al (1986) Cell 47, 545–554).

The extracellular domain of CD30 can be divided into six cysteine-rich protein motives of 40 amino acids (see FIG. 4) which, apart from the shortened motives 1B and 3B, each contain six cysteine radicals. As in the case of other members of the NGFR protein family, the positions of the cysteines in these sub-domains are highly conserved. There are also homologies to the corresponding regions of the following receptors: human insulin receptor-related receptor; Shier & Watt (1989), J. Biol. Chem. 264, 14605–14608); Transforming growth factor-β1 binding protein; Kanzaki et al (1990), Cell 61, 1051–1061); Mouse interleukin-3 receptor) Gorman et al (1990) Proc. Natl. Acad. Sci. USA 87, 5459–5463); sevenless protein of the fruit fly (Michael et al (1990) Proc. Natl. Acad. Sci. USA 87, 5351–5353).

At the DNA level there are homologies to other growth factor receptors, particularly the human fibroblast growth factor receptor-4 (Partanen et al (1991) EMBO J. 10, 1347–1354).

The results of comparisons between sequences, therefore, show that the CD30 antigen also is very probably a receptor for a growth factor. Consequently the nucleotide and protein sequences of CD30 provided by the invention can obviously be used for receptor studies, i.e. which factors can become bound to CD30, how—competitively or constitutively—the bond can be influenced, and what effects the bonding of the ligands have on the cell.

More particularly, the nucleotide sequence made available can be used to create transgenic animals for investigation of the receptor and the associated signal system.

We claim:

1. An isolated nucleic acid molecule comprising a polynucleotide having a sequence encoding the amino acid sequence of SEQ. ID. NO.: 2.

2. A recombinant vector comprising an isolated nucleic acid of claim 1.

3. A cell transformed with a recombinant vector of claim 2.

4. An isolated nucleic acid molecule comprising a polynucleotide having the nucleotide sequence of SEQ. ID. NO. 1.

5. A recombinant vector comprising an isolated nucleic acid of claim 4.

6. A cell transformed with a recombinant vector of claim 5.

7. A method for producing a CD30 protein comprising:
   i) culturing a transformed cell of claim 3 or 6; and
   ii) recovering CD30 protein produced by the cultured host cell.

8. A method for preparing a hybridization probe comprising:
   i) isolating a restriction fragment of the DNA molecule of claim 1 or claim 4 and its complementary strand;
   ii) nick-translating the restriction fragment of step (i) in the presence of a labeled nucleotide to obtain a labeled hybridization probe.

9. A hybridization probe prepared according to the method of claim 8.

10. An isolated nucleic acid molecule comprising a polynucleotide having a nucleotide sequence selected from the group consisting of
    a sequence encoding the portion of the amino acid sequence of SEQ. ID. NO. 2 from residue 19 to residue 379;
    a sequence encoding the portion of the amino acid sequence of SEQ. ID. NO. 2 from residue 408 to residue 595;
    a sequence encoding the portion of the amino acid sequence of SEQ. ID. NO. 2 from residue 19 to residue 93;
    a sequence encoding the portion of the amino acid sequence of SEQ. ID. NO. 2 from residue 112 to residue 416;
    the sequence from nucleotide 218 to nucleotide 1732 of SEQ. ID. NO. 1;
    the sequence from nucleotide 277 to nucleotide 1359 of SEQ. ID. NO. 1; and
    the sequence from nucleotide 1444 to nucleotide 2007 of SEQ. ID. NO. 1.

11. A recombinant vector comprising an isolated nucleic acid of claim 10.

12. A cell transformed with a recombinant vector of claim 11.

13. A hybridization probe comprising the nucleic acid of claim 1 or 10 and a label selected from the group consisting of radioactive atoms, stain groups, or epitopes introduced for systems based on light or enzymatic stain reactions for detection of nucleic acids.

14. An isolated nucleic acid molecule comprising a polynucleotide having a nucleotide sequence selected from the group consisting of
    portion I, which encodes a part of the amino acid sequence of SEQ. ID. NO. 2 between residue 19 and residue 93 that presents an epitope that is specifically bound by the Ki-1 monoclonal antibody;
    portion II, which encodes a part of the amino acid sequence of SEQ. ID. NO. 2 between residue 112 and residue 416 that presents an epitope that is specifically bound by the Ber-H2 monoclonal antibody; and
    portion III, which encodes a part of the amino acid sequence of SEQ. ID. NO. 2 between residue 19 and residue 416 and that presents an epitope that is specifically bound by the Ki-1 monoclonal antibody and an epitope that is specifically bound by the Ber-H2 monoclonal antibody.

15. A recombinant vector comprising an isolated nucleic acid of claim 14.

16. A cell transformed with a recombinant vector of claim 15.

17. An isolated nucleic acid encoding a fusion protein comprising a first polypeptide comprising an amino acid sequence selected from the group consisting of
    the portion of the amino acid sequence of SEQ. ID. NO. 2 from residue 19 to residue 379;
    the portion of the amino acid sequence of SEQ. ID. NO. 2 from residue 408 to residue 595;
    the amino acid sequence of SEQ. ID. NO. 2;
    the portion of SEQ. ID. NO. 2 between residue 19 and residue 263 that presents an epitope that is specifically bound by the Ki-1 monoclonal antibody;
    that portion of SEQ. ID. NO. 2 between residue 112 and residue 416 that presents an epitope that is specifically bound by the Ber-H2 monoclonal antibody; and
    that portion of SEQ. ID. NO. 2 between residue 19 and residue 416 and that presents an epitope that is specifically bound by the Ki-1 monoclonal antibody and an epitope that is specifically bound by the Ber-H2 monoclonal antibody;
    and a second polypeptide.

18. An isolated nucleic acid of claim 17, wherein said second polypeptide is a bacterial protein.

19. A recombinant vector comprising an isolated nucleic acid of claim 18.

20. A cell transformed with a recombinant vector of claim 19.

21. An isolated nucleic acid of claim 17, wherein said second polypeptide is β-galactosidase.

22. A recombinant vector comprising an isolated nucleic acid of claim 21.

23. A cell transformed with a recombinant vector of claim 22.

24. A recombinant vector comprising an isolated nucleic acid of claim 17.

25. A cell transformed with a recombinant vector of claim 24.

26. An isolated nucleic acid encoding a fusion protein comprising (1) the extracellular portion of human CD30 consisting essentially of residues 19 to 379 of SEQ. ID. NO. 2 and (2) a second polypeptide.

27. A recombinant vector comprising an isolated nucleic acid of claim 26.

28. A cell transformed with a recombinant vector of claim 27.

29. A recombinant vector according to any one of claims 2, 5, 11, 15, 19, 22, 24 and 27 which further comprises an inducible promoter.

30. A transformed cell of any one of claims 3, 6, 12, 16, 20, 23, 25 and 28 that is a eukaryotic cell.

31. A transformed cell of claim 30 that is a mammalian cell.

32. A method for producing a CD30 protein, a portion of a CD30 protein, or a fusion protein comprising a CD30 protein or comprising a portion of CD30 protein, comprising:

i) culturing a transformed cell of any one of claims 12, 16, 20, 23, 25 and 28; and ii) recovering CD30 protein produced by the cultured host cell.

\* \* \* \* \*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 3627 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( v i ) ORIGINAL SOURCE:
( A ) ORGANISM: Homo sapiens ( i x ) FEATURE:
( A ) NAME/KEY: CDS
( B ) LOCATION: 223..2010

( x i ) SEQUENCE DESCRIPTION: SEQ ID NO:1:

```
ATACGGAGA  ACTAAGGCTG  AAACCTCGGA  GGAACAACCA  CTTTTGAAGT  GACTTCGCGG                              60

CGTGCGTTGG  GTGCGGACTA  GGTGGCCCCG  GCGGGAGTGT  GCTGGAGCCT  GAAGTCCACG                            120

CGCGCGGCTG  AGAACCGCCG  GGACCGCACG  TGGGCGCCGC  GCGCTTCCCC  CGCTTCCCAG                            180

GTGGGCGCCG  GCCGCCAGGC  CACCTCACGT  CCGGCCCCGG  GG  ATG  CGC  GTC  CTC                            234
                                                    Met  Arg  Val  Leu
                                                      1

CTC  GCC  GCG  CTG  GGA  CTG  CTG  TTC  CTG  GGG  GCG  CTA  CGA  GCC  TTC  CCA                   282
Leu  Ala  Ala  Leu  Gly  Leu  Leu  Phe  Leu  Gly  Ala  Leu  Arg  Ala  Phe  Pro
  5               10                      15                      20

CAG  GAT  CGA  CCC  TTC  GAG  GAC  ACC  TGT  CAT  GGA  AAC  CCC  AGC  CAC  TAC                   330
Gln  Asp  Arg  Pro  Phe  Glu  Asp  Thr  Cys  His  Gly  Asn  Pro  Ser  His  Tyr
                     25                      30                      35

TAT  GAC  AAG  GCT  GTC  AGG  AGG  TGC  TGT  TAC  CGC  TGC  CCC  ATG  GGG  CTG                   378
Tyr  Asp  Lys  Ala  Val  Arg  Arg  Cys  Cys  Tyr  Arg  Cys  Pro  Met  Gly  Leu
            40                      45                      50

TTC  CCG  ACA  CAG  CAG  TGC  CCA  CAG  AGG  CCT  ACT  GAC  TGC  AGG  AAG  CAG                   426
Phe  Pro  Thr  Gln  Gln  Cys  Pro  Gln  Arg  Pro  Thr  Asp  Cys  Arg  Lys  Gln
        55                      60                      65

TGT  GAG  CCT  GAC  TAC  TAC  CTG  GAT  GAG  GCC  GAC  CGC  TGT  ACA  GCC  TGC                   474
Cys  Glu  Pro  Asp  Tyr  Tyr  Leu  Asp  Glu  Ala  Asp  Arg  Cys  Thr  Ala  Cys
```

-continued

```
             70                         75                         80
GTG ACT TGT TCT CGA GAT GAC CTC GTG GAG AAG ACG CCG TGT GCA TGG                  522
Val Thr Cys Ser Arg Asp Asp Leu Val Glu Lys Thr Pro Cys Ala Trp
85              90                      95                     100

AAC TCC TCC CGT GTC TGC GAA TGT CGA CCC GGC ATG TTC TGT TCC ACG                  570
Asn Ser Ser Arg Val Cys Glu Cys Arg Pro Gly Met Phe Cys Ser Thr
                105                     110                     115

TCT GCC GTC AAC TCC TGT GCC CGC TGC TTC TTC CAT TCT GTC TGT CCG                  618
Ser Ala Val Asn Ser Cys Ala Arg Cys Phe Phe His Ser Val Cys Pro
            120                     125                     130

GCA GGG ATG ATT GTC AAG TTC CCA GGC ACG GCG CAG AAG AAC ACG GTC                  666
Ala Gly Met Ile Val Lys Phe Pro Gly Thr Ala Gln Lys Asn Thr Val
        135                     140                     145

TGT GAG CCG GCT TCC CCA GGG GTC AGC CCT GCC TGT GCC AGC CCA GAG                  714
Cys Glu Pro Ala Ser Pro Gly Val Ser Pro Ala Cys Ala Ser Pro Glu
    150                     155                     160

AAC TGC AAG GAA CCC TCC AGT GGC ACC ATC CCC CAG GCC AAG CCC ACC                  762
Asn Cys Lys Glu Pro Ser Ser Gly Thr Ile Pro Gln Ala Lys Pro Thr
165                     170                     175                     180

CCG GTG TCC CCA GCA ACC TCC AGT GCC AGC ACC ATG CCT GTA AGA GGG                  810
Pro Val Ser Pro Ala Thr Ser Ser Ala Ser Thr Met Pro Val Arg Gly
                185                     190                     195

GGC ACC CGC CTC GCC CAG GAA GCT GCT TCT AAA CTG ACG AGG GCT CCC                  858
Gly Thr Arg Leu Ala Gln Glu Ala Ala Ser Lys Leu Thr Arg Ala Pro
            200                     205                     210

GAC TCT CCC TCC TCT GTG GGA AGG CCT AGT TCA GAT CCA GGT CTG TCC                  906
Asp Ser Pro Ser Ser Val Gly Arg Pro Ser Ser Asp Pro Gly Leu Ser
        215                     220                     225

CCA ACA CAG CCA TGC CCA GAG GGG TCT GGT GAT TGC AGA AAG CAG TGT                  954
Pro Thr Gln Pro Cys Pro Glu Gly Ser Gly Asp Cys Arg Lys Gln Cys
    230                     235                     240

GAG CCC GAC TAC TAC CTG GAC GAG GCC GGC CGC TGC ACA GCC TGC GTG                 1002
Glu Pro Asp Tyr Tyr Leu Asp Glu Ala Gly Arg Cys Thr Ala Cys Val
245                     250                     255                     260

AGC TGT TCT CGA GAT GAC CTT GTG GAG AAG ACG CCA TGT GCA TGG AAC                 1050
Ser Cys Ser Arg Asp Asp Leu Val Glu Lys Thr Pro Cys Ala Trp Asn
                265                     270                     275

TCC TCC CGC ACC TGC GAA TGT CGA CCT GGC ATG ATC TGT GCC ACA TCA                 1098
Ser Ser Arg Thr Cys Glu Cys Arg Pro Gly Met Ile Cys Ala Thr Ser
            280                     285                     290

GCC ACC AAC TCC TGT GCC CGC TGT GTC CCC TAC CCA ATC TGT GCA GCA                 1146
Ala Thr Asn Ser Cys Ala Arg Cys Val Pro Tyr Pro Ile Cys Ala Ala
        295                     300                     305

GAG ACG GTC ACC AAG CCC CAG GAT ATG GCT GAG AAG GAC ACC ACC TTT                 1194
Glu Thr Val Thr Lys Pro Gln Asp Met Ala Glu Lys Asp Thr Thr Phe
    310                     315                     320

GAG GCG CCA CCC CTG GGG ACC CAG CCG GAC TGC AAC CCC ACC CCA GAG                 1242
Glu Ala Pro Pro Leu Gly Thr Gln Pro Asp Cys Asn Pro Thr Pro Glu
325                     330                     335                     340

AAT GGC GAG GCG CCT GCC AGC ACC AGC CCC ACT CAG AGC TTG CTG GTG                 1290
Asn Gly Glu Ala Pro Ala Ser Thr Ser Pro Thr Gln Ser Leu Leu Val
                345                     350                     355

GAC TCC CAG GCC AGT AAG ACG CTG CCC ATC CCA ACC AGC GCT CCC GTC                 1338
Asp Ser Gln Ala Ser Lys Thr Leu Pro Ile Pro Thr Ser Ala Pro Val
            360                     365                     370

GCT CTC TCC TCC ACG GGG AAG CCC GTT CTG GAT GCA GGG CCA GTG CTC                 1386
Ala Leu Ser Ser Thr Gly Lys Pro Val Leu Asp Ala Gly Pro Val Leu
        375                     380                     385

TTC TGG GTG ATC CTG GTG TTG GTT GTG GTG GTC GGC TCC AGC GCC TTC                 1434
Phe Trp Val Ile Leu Val Leu Val Val Val Val Gly Ser Ser Ala Phe
```

```
                390                            395                            400
CTC   CTG   TGC   CAC   CGG   AGG   GCC   TGC   AGG   AAG   CGA   ATT   CGG   CAG   AAG   CTC          1482
Leu   Leu   Cys   His   Arg   Arg   Ala   Cys   Arg   Lys   Arg   Ile   Arg   Gln   Lys   Leu
405               410                           415                           420

CAC   CTG   TGC   TAC   CCG   GTC   CAG   ACC   TCC   CAG   CCC   AAG   CTA   GAG   CTT   GTG          1530
His   Leu   Cys   Tyr   Pro   Val   Gln   Thr   Ser   Gln   Pro   Lys   Leu   Glu   Leu   Val
                        425                           430                           435

GAT   TCC   AGA   CCC   AGG   AGG   AGC   TCA   ACG   CAG   CTG   AGG   AGT   GGT   GCG   TCG          1578
Asp   Ser   Arg   Pro   Arg   Arg   Ser   Ser   Thr   Gln   Leu   Arg   Ser   Gly   Ala   Ser
                  440                           445                           450

GTG   ACA   GAA   CCC   GTC   GCG   GAA   GAG   CGA   GGG   TTA   ATG   AGC   CAG   CCA   CTG          1626
Val   Thr   Glu   Pro   Val   Ala   Glu   Glu   Arg   Gly   Leu   Met   Ser   Gln   Pro   Leu
            455                           460                           465

ATG   GAG   ACC   TGC   CAC   AGC   GTG   GGG   GCA   GCC   TAC   CTG   GAG   AGC   CTG   CCG          1674
Met   Glu   Thr   Cys   His   Ser   Val   Gly   Ala   Ala   Tyr   Leu   Glu   Ser   Leu   Pro
      470                           475                           480

CTG   CAG   GAT   GCC   AGC   CCG   GCC   GGG   GGC   CCC   TCG   TCC   CCC   AGG   GAC   CTT          1722
Leu   Gln   Asp   Ala   Ser   Pro   Ala   Gly   Gly   Pro   Ser   Ser   Pro   Arg   Asp   Leu
485                           490                           495                           500

CCT   GAG   CCC   CGG   GTG   TCC   ACG   GAG   CAC   ACC   AAT   AAC   AAG   ATT   GAG   AAA          1770
Pro   Glu   Pro   Arg   Val   Ser   Thr   Glu   His   Thr   Asn   Asn   Lys   Ile   Glu   Lys
                        505                           510                           515

ATC   TAC   ATC   ATG   AAG   GCT   GAC   ACC   GTG   ATC   GTG   GGG   ACC   GTG   AAG   GCT          1818
Ile   Tyr   Ile   Met   Lys   Ala   Asp   Thr   Val   Ile   Val   Gly   Thr   Val   Lys   Ala
                  520                           525                           530

GAG   CTG   CCG   GAG   GGC   CGG   GGC   CTG   GCG   GGG   CCA   GCA   GAG   CCC   GAG   TTG          1866
Glu   Leu   Pro   Glu   Gly   Arg   Gly   Leu   Ala   Gly   Pro   Ala   Glu   Pro   Glu   Leu
            535                           540                           545

GAG   GAG   GAG   CTG   GAG   GCG   GAC   CAT   ACC   CCC   CAC   TAC   CCC   GAG   CAG   GAG          1914
Glu   Glu   Glu   Leu   Glu   Ala   Asp   His   Thr   Pro   His   Tyr   Pro   Glu   Gln   Glu
      550                           555                           560

ACA   GAA   CCG   CCT   CTG   GGC   AGC   TGC   AGC   GAT   GTC   ATG   CTC   TCA   GTG   GAA          1962
Thr   Glu   Pro   Pro   Leu   Gly   Ser   Cys   Ser   Asp   Val   Met   Leu   Ser   Val   Glu
565                           570                           575                           580

GAG   GAA   GGG   AAA   GAA   GAC   CCC   TTG   CCC   ACA   GCT   GCC   TCT   GGA   AAG   TGA          2010
Glu   Glu   Gly   Lys   Glu   Asp   Pro   Leu   Pro   Thr   Ala   Ala   Ser   Gly   Lys   *
                        585                           590                           595

GGCCTGGGCT   GGGCTGGGGC   TAGGAGGGCA   GCAGGGTGGC   CTCTGGGAGG   CCAGGATGGC                            2070

ACTGTTGGCA   CCGAGGTTGG   GGGCAGAGGC   CCATCTGGCC   TGAACTGAGG   CTCCAGCATC                            2130

TAGTGGTGGA   CCGGCCGGTC   ACTGCAGGGG   TCTGGTGGTC   TCTGCTTGCA   TCCCCAACTT                            2190

AGCTGTCCCC   TGACCCAGAG   CCTAGGGGAT   CCGGGGCTTG   TACAGAAGAG   ACAGTCCAAG                            2250

GGGACTGGAT   CCCAGCAGTG   ATGTTGGTTG   AGGCAGCAAA   CAGATGGCAG   GATGGGCACT                            2310

GCCGAGAACA   GCATTGGTCC   CAGAGCCCTG   GGCATCAGAC   CTTAACCACC   AGGCCCACAG                            2370

CCCAGCGAGG   GAGAGGTCGT   GAGGCCAGCT   CCCGGGGCCC   CTGTAACCCT   ACTCTCCTCT                            2430

CTCCCTGGAC   CTCAGAGGTG   ACACCCATTG   GGCCCTTCCG   GCATGCCCCC   AGTTACTGTA                            2490

AATGTGGCCC   CCAGTGGGCA   TGGAGCCAGT   GCCTGTGGTT   GTTTCTCCAG   AGTCAAAAGG                            2550

GAAGTCGAGG   GATGGGCGT    CGTCAGCTGG   CACTGTCTCT   GCTGCAGCGG   CCACACTGTA                            2610

CTCTGCACTG   GTGTGAGGGC   CCCTGCCTGG   ACTGTGGGAC   CCTCCTGGTG   CTGCCCACCT                            2670

TCCCTGTCCT   GTAGCCCCCT   CGGTGGGCCC   AGGGCCTAGG   GGCCCAGGAT   CAAGTCACTC                            2730

ATCTCAGAAT   GTCCCCACCA   ATCCCCGCCA   CAGCAGGCGC   CTCGGGTCCC   AGATGTCTGC                            2790

AGCCCTCAGC   AGCTGCAGAC   CGCCCCTCAC   CAACCCAGAG   AACCTGCTTT   ACTTTGCCCA                            2850

GGGACTTCCT   CCCCATGTGA   ACATGGGGAA   CTTCGGGCCC   TGCCTGGAGT   CCTTGACCGC                            2910
```

| | | | | | |
|---|---|---|---|---|---|
| TCTCTGTGGG | CCCCACCCAC | TCTGTCCTGG | GAAATGAAGA | AGCATCTTCC | TTAGGTCTGC | 2970
| CCTGCTTGCA | AATCCACTAG | CACCGACCCC | ACCACCTGGT | TCCGGCTCTG | CACGCTTTGG | 3030
| GGTGTGGATG | TCGAGAGGCA | CCACGGCCTC | ACCCAGGCAT | CTGCTTTACT | CTGGACCATA | 3090
| GGAAACAAGA | CCGTTTGGAG | GTTTCATCAG | GATTTTGGGT | TTTTCACATT | TCACGCTAAG | 3150
| GAGTAGTGGC | CCTGACTTCC | GGTCGGCTGG | CCAGCTGACT | CCCTAGGGCC | TTCAGACGTG | 3210
| TATGCAAATG | AGTGATGGAT | AAGGATGAGT | CTTGGAGTTG | CGGGCAGCCT | GGAGACTCGT | 3270
| GGACTTACCG | CCTGGAGGCA | GGCCCGGGAA | GGCTGCTGTT | TACTCATCGG | GCAGCCACGT | 3330
| GCTCTCTGGA | GGAAGTGATA | GTTTCTGAAA | CCGCTCAGAT | GTTTTGGGGA | AAGTTGGAGA | 3390
| AGCCGTGGCC | TTGCGAGAGG | TGGTTACACC | AGAACCTGGA | CATTGGCCAG | AAGAAGCTTA | 3450
| AGTGGGCAGA | CACTGTTTGC | CCAGTGTTTG | TGCAAGGATG | GAGTGGGTGT | CTCTGCATCA | 3510
| CCCACAGCCG | CAGCTGTAAG | GCACGCTGGA | AGGCACACGC | CTGCCAGGCA | GGGCAGTCTG | 3570
| GCGCCCATGA | TGGGAGGGAT | TGACATGTTT | CAACAAAATA | ATGCACTTCC | TTAAAAA | 3627

(2) INFORMATION FOR SEQ ID NO:2:

(i) SEQUENCE CHARACTERISTICS:
        (A) LENGTH: 595 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Val Leu Leu Ala Ala Leu Gly Leu Leu Phe Leu Gly Ala Leu
 1               5                  10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
    50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240
```

```
Arg  Lys  Gln  Cys  Glu  Pro  Asp  Tyr  Tyr  Leu  Asp  Glu  Ala  Gly  Arg  Cys
               245                      250                          255

Thr  Ala  Cys  Val  Ser  Cys  Ser  Arg  Asp  Asp  Leu  Val  Glu  Lys  Thr  Pro
                    260                 265                     270

Cys  Ala  Trp  Asn  Ser  Ser  Arg  Thr  Cys  Glu  Cys  Arg  Pro  Gly  Met  Ile
               275                 280                     285

Cys  Ala  Thr  Ser  Ala  Thr  Asn  Ser  Cys  Ala  Arg  Cys  Val  Pro  Tyr  Pro
     290                      295                     300

Ile  Cys  Ala  Ala  Glu  Thr  Val  Thr  Lys  Pro  Gln  Asp  Met  Ala  Glu  Lys
305                      310                 315                          320

Asp  Thr  Thr  Phe  Glu  Ala  Pro  Pro  Leu  Gly  Thr  Gln  Pro  Asp  Cys  Asn
                    325                      330                     335

Pro  Thr  Pro  Glu  Asn  Gly  Glu  Ala  Pro  Ala  Ser  Thr  Ser  Pro  Thr  Gln
               340                      345                          350

Ser  Leu  Leu  Val  Asp  Ser  Gln  Ala  Ser  Lys  Thr  Leu  Pro  Ile  Pro  Thr
          355                      360                     365

Ser  Ala  Pro  Val  Ala  Leu  Ser  Ser  Thr  Gly  Lys  Pro  Val  Leu  Asp  Ala
     370                      375                     380

Gly  Pro  Val  Leu  Phe  Trp  Val  Ile  Leu  Val  Leu  Val  Val  Val  Val  Gly
385                      390                     395                          400

Ser  Ser  Ala  Phe  Leu  Cys  His  Arg  Arg  Ala  Cys  Arg  Lys  Arg  Ile
                    405                 410                     415

Arg  Gln  Lys  Leu  His  Leu  Cys  Tyr  Pro  Val  Gln  Thr  Ser  Gln  Pro  Lys
               420                 425                     430

Leu  Glu  Leu  Val  Asp  Ser  Arg  Pro  Arg  Arg  Ser  Ser  Thr  Gln  Leu  Arg
          435                      440                     445

Ser  Gly  Ala  Ser  Val  Thr  Glu  Pro  Val  Ala  Glu  Glu  Arg  Gly  Leu  Met
     450                      455                     460

Ser  Gln  Pro  Leu  Met  Glu  Thr  Cys  His  Ser  Val  Gly  Ala  Ala  Tyr  Leu
465                      470                     475                          480

Glu  Ser  Leu  Pro  Leu  Gln  Asp  Ala  Ser  Pro  Ala  Gly  Gly  Pro  Ser  Ser
                    485                      490                     495

Pro  Arg  Asp  Leu  Pro  Glu  Pro  Arg  Val  Ser  Thr  Glu  His  Thr  Asn  Asn
               500                      505                     510

Lys  Ile  Glu  Lys  Ile  Tyr  Ile  Met  Lys  Ala  Asp  Thr  Val  Ile  Val  Gly
          515                      520                     525

Thr  Val  Lys  Ala  Glu  Leu  Pro  Glu  Gly  Arg  Gly  Leu  Ala  Gly  Pro  Ala
     530                      535                     540

Glu  Pro  Glu  Leu  Glu  Glu  Glu  Leu  Glu  Ala  Asp  His  Thr  Pro  His  Tyr
545                      550                     555                          560

Pro  Glu  Gln  Glu  Thr  Glu  Pro  Pro  Leu  Gly  Ser  Cys  Ser  Asp  Val  Met
               565                      570                     575

Leu  Ser  Val  Glu  Glu  Glu  Gly  Lys  Glu  Asp  Pro  Leu  Pro  Thr  Ala  Ala
               580                      585                     590

Ser  Gly  Lys
          595
```

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
            ( A ) ORGANISM: Homo sapiens ( x i ) SEQUENCE DESCRIPTION: SEQ ID NO:3:

TTCCCACAGG ATCGACCC                                                                                               18

( 2 ) INFORMATION FOR SEQ ID NO:4:

( i ) SEQUENCE CHARACTERISTICS:
            ( A ) LENGTH: 14 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
            ( A ) ORGANISM: Homo sapiens ( x i ) SEQUENCE DESCRIPTION: SEQ ID NO:4:

CTCCCACGGG GAAG                                                                                                   14

( 2 ) INFORMATION FOR SEQ ID NO:5:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
            ( A ) ORGANISM: Homo sapiens ( x i ) SEQUENCE DESCRIPTION: SEQ ID NO:5:

CACCGGAGGG CCTGCA                                                                                                 16

( 2 ) INFORMATION FOR SEQ ID NO:6:

( i ) SEQUENCE CHARACTERISTICS:
            ( A ) LENGTH: 14 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
            ( A ) ORGANISM: Homo sapiens ( x i ) SEQUENCE DESCRIPTION: SEQ ID NO:6:

CTGCCTCTGG AAAG                                                                                                   14

( 2 ) INFORMATION FOR SEQ ID NO:7:

( i ) SEQUENCE CHARACTERISTICS:

(A) LENGTH: 122 amino acids
(B) TYPE: amino acid
(C) STRANDEDNESS: Not Relevant
(D) TOPOLOGY: linear (ii) MOLECULE TYPE: protein (iii) HYPOTHETICAL: NO (v) FRAGMENT TYPE: internal (ix) FEATURE:
(A) NAME/KEY: Protein
(B) LOCATION: 1..122
(D) OTHER INFORMATION: /note= "CD30 (1A), see Fig. 5"

(xi) SEQUENCE DESCRIPTION: SEQ ID NO:7:

| Thr | Cys | His | Gly | Asn | Pro | Ser | Pro | Tyr | Tyr | Asp | Lys | Ala | Val | Arg | Arg |
| 1 | | | | 5 | | | | | 10 | | | | | 15 | |

| Cys | Cys | Tyr | Arg | Cys | Pro | Met | Gly | Leu | Phe | Pro | Thr | Gln | Gln | Cys | Pro |
| | | | 20 | | | | | 25 | | | | | 30 | | |

| Gln | Arg | Pro | Thr | Asp | Cys | Arg | Gln | Cys | Glu | Pro | Asp | Tyr | Tyr | Leu | Asp |
| | | | 35 | | | | | 40 | | | | | 45 | | |

| Glu | Ala | Asp | Arg | Cys | Thr | Ala | Cys | Val | Thr | Cys | Ser | Arg | Asp | Asp | Leu |
| | | 50 | | | | | 55 | | | | | 60 | | | |

| Val | Glu | Lys | Thr | Pro | Cys | Ala | Trp | Asn | Ser | Ser | Arg | Val | Cys | Glu | Cys |
| 65 | | | | | 70 | | | | | 75 | | | | | 80 |

| Arg | Pro | Gly | Met | Phe | Cys | Ser | Thr | Ser | Ala | Val | Asn | Ser | Cys | Ala | Arg |
| | | | | 85 | | | | | 90 | | | | | 95 | |

| Cys | Phe | Phe | His | Ser | Val | Cys | Pro | Ala | Gly | Met | Ile | Val | Lys | Phe | Pro |
| | | | | 100 | | | | | 105 | | | | | 110 | |

| Gly | Thr | Ala | Gln | Lys | Asn | Thr | Val | Cys | Glu |
| | | | 115 | | | | | 120 | |

(2) INFORMATION FOR SEQ ID NO:8:

(i) SEQUENCE CHARACTERISTICS:
(A) LENGTH: 120 amino acids
(B) TYPE: amino acid
(C) STRANDEDNESS: Not Relevant
(D) TOPOLOGY: linear (ii) MOLECULE TYPE: protein (iii) HYPOTHETICAL: NO (v) FRAGMENT TYPE: internal (ix) FEATURE:
(A) NAME/KEY: Protein
(B) LOCATION: 1..120
(D) OTHER INFORMATION: /note= "CD30 (1B), see Fig. 5"

(xi) SEQUENCE DESCRIPTION: SEQ ID NO:8:

| Ala | Ser | Lys | Leu | Thr | Arg | Ala | Pro | Asp | Ser | Pro | Ser | Ser | Val | Gly | Arg |
| 1 | | | | 5 | | | | | 10 | | | | | 15 | |

| Pro | Ser | Ser | Asp | Pro | Gly | Leu | Ser | Pro | Thr | Gln | Pro | Cys | Pro | Glu | Gly |
| | | | 20 | | | | | 25 | | | | | 30 | | |

| Ser | Gly | Asp | Cys | Arg | Gln | Cys | Glu | Pro | Asp | Tyr | Tyr | Leu | Asp | Glu | Ala |
| | | | 35 | | | | | 40 | | | | | 45 | | |

| Gly | Arg | Cys | Thr | Ala | Cys | Val | Ser | Cys | Ser | Arg | Asp | Asp | Leu | Val | Glu |
| | | 50 | | | | | 55 | | | | | 60 | | | |

| Lys | Thr | Pro | Cys | Ala | Trp | Asn | Ser | Ser | Arg | Thr | Cys | Glu | Cys | Arg | Pro |
| 65 | | | | | 70 | | | | | 75 | | | | | 80 |

| Gly | Met | Ile | Cys | Ala | Thr | Ser | Ala | Thr | Asn | Ser | Cys | Ala | Arg | Cys | Val |

|  |  |  |  | 85 |  |  |  |  | 90 |  |  |  |  | 95 |  |
|--|--|--|--|--|--|--|--|--|--|--|--|--|--|--|--|
| Pro | Tyr | Pro | Ile<br>100 | Cys | Ala | Ala | Glu | Thr<br>105 | Val | Thr | Lys | Pro | Gln<br>110 | Asp | Met |
| Ala | Glu | Lys<br>115 | Asp | Thr | Thr | Phe | Glu<br>120 |

(2) INFORMATION FOR SEQ ID NO:9:

(i) SEQUENCE CHARACTERISTICS:
        (A) LENGTH: 164 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (v) FRAGMENT TYPE: internal (ix) FEATURE:
        (A) NAME/KEY: Protein
        (B) LOCATION: 1..164
        (D) OTHER INFORMATION: /note= "TNFR2, see Fig. 5"

(xi) SEQUENCE DESCRIPTION: SEQ ID NO:9:

| Thr<br>1 | Cys | Arg | Leu | Arg<br>5 | Leu | Glu | Tyr | Tyr | Asp<br>10 | Gln | Thr | Ala | Gln | Met<br>15 | Cys |
|--|--|--|--|--|--|--|--|--|--|--|--|--|--|--|--|
| Cys | Ser | Lys | Cys<br>20 | Ser | Pro | Gly | Gln | His<br>25 | Ala | Lys | Val | Phe | Cys<br>30 | Thr | Lys |
| Thr | Ser | Asp<br>35 | Thr | Val | Cys | Asp | Ser<br>40 | Cys | Glu | Asp | Ser | Thr<br>45 | Tyr | Thr | Gln |
| Leu | Trp<br>50 | Asn | Trp | Val | Pro | Glu<br>55 | Cys | Leu | Ser | Cys | Gly<br>60 | Ser | Arg | Cys | Ser |
| Ser<br>65 | Asp | Gln | Val | Glu | Thr<br>70 | Gln | Ala | Cys | Thr | Arg<br>75 | Glu | Gln | Asn | Arg | Ile<br>80 |
| Cys | Thr | Cys | Arg | Pro<br>85 | Gly | Trp | Tyr | Cys | Ala<br>90 | Leu | Ser | Lys | Gln | Glu<br>95 | Gly |
| Cys | Arg | Leu | Cys<br>100 | Ala | Pro | Leu | Arg | Lys<br>105 | Cys | Arg | Pro | Gly | Phe<br>110 | Gly | Val |
| Ala | Arg | Pro<br>115 | Gly | Thr | Glu | Thr | Ser<br>120 | Asp | Val | Val | Cys | Lys<br>125 | Pro | Cys | Ala |
| Pro | Gly<br>130 | Thr | Phe | Ser | Asn | Thr<br>135 | Thr | Ser | Ser | Thr | Asp<br>140 | Ile | Cys | Arg | Pro |
| His | Gln<br>145 | Ile | Cys | Asn | Val<br>150 | Val | Ala | Ile | Pro | Gly<br>155 | Asn | Ala | Ser | Met | Asp<br>160 |
| Ala | Val | Cys | Thr |

(2) INFORMATION FOR SEQ ID NO:10:

(i) SEQUENCE CHARACTERISTICS:
        (A) LENGTH: 154 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (v) FRAGMENT TYPE: internal (ix) FEATURE:
        (A) NAME/KEY: Protein
        (B) LOCATION: 1..154

(D) OTHER INFORMATION: /note= "TNFR1, see Fig. 5"

(xi) SEQUENCE DESCRIPTION: SEQ ID NO:10:

| Val | Cys | Pro | Gln | Gly | Lys | Tyr | Ile | His | Pro | Gln | Asn | Asn | Ser | Ile | Cys |
|---|---|---|---|---|---|---|---|---|---|---|---|---|---|---|---|
| 1 | | | | 5 | | | | | 10 | | | | | 15 | |
| Cys | Thr | Lys | Cys | His | Lys | Gly | Thr | Tyr | Leu | Tyr | Asn | Asp | Cys | Pro | Gly |
| | | | 20 | | | | 25 | | | | | | 30 | | |
| Pro | Gly | Gln | Asp | Thr | Asp | Cys | Asp | Glu | Cys | Glu | Ser | Gln | Ser | Phe | Thr |
| | | 35 | | | | | 40 | | | | | 45 | | | |
| Ala | Ser | Glu | Asn | His | Leu | Arg | His | Cys | Leu | Ser | Cys | Ser | Lys | Cys | Arg |
| | 50 | | | | | 55 | | | | | 60 | | | | |
| Lys | Glu | Met | Gly | Gln | Val | Glu | Ile | Ser | Ser | Cys | Thr | Val | Asp | Arg | Asp |
| 65 | | | | | 70 | | | | | 75 | | | | | 80 |
| Thr | Val | Cys | Gly | Cys | Arg | Lys | Asn | Gln | Tyr | Arg | His | Tyr | Trp | Ser | Glu |
| | | | | 85 | | | | | 90 | | | | | 95 | |
| Asn | Leu | Phe | Gln | Cys | Phe | Asn | Cys | Ser | Leu | Cys | Leu | Asn | Gly | Thr | Val |
| | | | 100 | | | | | 105 | | | | | 110 | | |
| His | Leu | Ser | Gly | Gln | Glu | Lys | Gln | Asn | Thr | Val | Cys | Thr | Cys | His | Ala |
| | | 115 | | | | | 120 | | | | | 125 | | | |
| Gly | Phe | Phe | Leu | Arg | Glu | Asn | Glu | Cys | Val | Ser | Cys | Gly | Asn | Cys | Lys |
| | 130 | | | | | 135 | | | | | 140 | | | | |
| Lys | Ser | Leu | Glu | Cys | Thr | Lys | Leu | Cys | Leu | | | | | | |
| 145 | | | | | 150 | | | | | | | | | | |

(2) INFORMATION FOR SEQ ID NO:11:

(i) SEQUENCE CHARACTERISTICS:
        (A) LENGTH: 159 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (v) FRAGMENT TYPE: internal (ix) FEATURE:
        (A) NAME/KEY: Protein
        (B) LOCATION: 1..159
        (D) OTHER INFORMATION: /note= "NGFR, see Fig. 5"

(xi) SEQUENCE DESCRIPTION: SEQ ID NO:11:

| Ala | Cys | Pro | Thr | Gly | Leu | Tyr | Thr | His | Ser | Gly | Glu | Cys | Cys | Lys | Ala |
|---|---|---|---|---|---|---|---|---|---|---|---|---|---|---|---|
| 1 | | | | 5 | | | | | 10 | | | | | 15 | |
| Cys | Asn | Leu | Gly | Glu | Gly | Val | Ala | Gln | Pro | Cys | Gly | Ala | Asn | Gln | Thr |
| | | | 20 | | | | 25 | | | | | | 30 | | |
| Val | Cys | Glu | Pro | Cys | Leu | Asp | Asn | Val | Thr | Phe | Ser | Asp | Val | Val | Ser |
| | | 35 | | | | | 40 | | | | | 45 | | | |
| Ala | Thr | Glu | Pro | Cys | Lys | Pro | Cys | Thr | Glu | Cys | Leu | Gly | Leu | Gln | Ser |
| | 50 | | | | | 55 | | | | | 60 | | | | |
| Met | Ser | Ala | Pro | Cys | Val | Glu | Ala | Asp | Asp | Ala | Val | Cys | Arg | Cys | Ala |
| 65 | | | | | 70 | | | | | 75 | | | | | 80 |
| Tyr | Gly | Tyr | Tyr | Gln | Asp | Glu | Thr | Thr | Gly | His | Cys | Glu | Ala | Cys | Ser |
| | | | | 85 | | | | | 90 | | | | | 95 | |
| Val | Cys | Glu | Val | Gly | Ser | Gly | Leu | Val | Phe | Ser | Cys | Gln | Asp | Lys | Gln |
| | | | 100 | | | | | 105 | | | | | 110 | | |
| Asn | Thr | Val | Cys | Glu | Glu | Cys | Pro | Asp | Gly | Thr | Tyr | Ser | Asp | Glu | Ala |
| | | 115 | | | | | 120 | | | | | 125 | | | |

-continued

```
Asn  His  Val  Asp  Pro  Cys  Leu  Pro  Cys  Thr  Val  Cys  Glu  Asp  Thr  Glu
     130                 135                      140

Arg  Gln  Leu  Arg  Glu  Cys  Thr  Arg  Trp  Ala  Asp  Ala  Glu  Cys  Glu
145                      150                      155
```